United States Patent

Strömmer

[11] Patent Number: 5,267,295
[45] Date of Patent: Nov. 30, 1993

[54] METHODS AND DEVICE RELATED TO AUTOMATIC EXPOSURE IN X-RAY DIAGNOSTICS IN PARTICULAR IN MAMMOGRAPHY

[75] Inventor: Pekka Strömmer, Espoo, Finland

[73] Assignee: Planmed Oy, Finland

[21] Appl. No.: 898,503

[22] Filed: Jun. 15, 1992

Related U.S. Application Data

[63] Continuation of Ser. No. 616,058, Nov. 20, 1990, abandoned.

[30] Foreign Application Priority Data

Nov. 23, 1989 [FI] Finland ................. 895610

[51] Int. Cl.⁵ .............................. H05G 1/44
[52] U.S. Cl. ........................ 378/97; 378/108
[58] Field of Search ..................... 378/97, 108

[56] References Cited

U.S. PATENT DOCUMENTS

| | | |
|---|---|---|
| 4,313,055 | 1/1982 | Richter . |
| 4,454,606 | 6/1984 | Relihan ............ 378/97 |
| 4,504,962 | 3/1985 | Moore . |
| 4,748,648 | 5/1988 | Boucle ............. 378/97 |
| 4,748,649 | 5/1988 | Griesmer et al. ...... 378/97 |
| 4,935,945 | 6/1990 | Mochizuki et al. ..... 378/97 |

FOREIGN PATENT DOCUMENTS 0077471 4/1983 European Pat. Off. .
1374610 11/1974 United Kingdom .

Primary Examiner—Craig E. Church
Attorney, Agent, or Firm—Jones & Askew

[57] ABSTRACT

Method in x-ray diagnostics for regulating the exposure of a film or equivalent to an optimal level. The radiation that has passed through an object is measured by detectors and, based on this measurement, the time of exposure regulated. The measurement signals are passed from the detector or from different detectors to an amplifier associated with each detector. The amplifications of the amplifiers are initially calibrated by exposing a reference object to a predetermined dosage, passing the amplified signals from the detectors one at a time to an integrator for an initial switching period, comparing each amplified and integrated signal with a reference value, and independently adjusting the switching period of each amplified signal to produce amplification values so that each detector and amplifier gives an integrated signal equal to the reference value.

3 Claims, 3 Drawing Sheets

METHODS AND DEVICE RELATED TO AUTOMATIC EXPOSURE IN X-RAY DIAGNOSTICS IN PARTICULAR IN MAMMOGRAPHY

CROSS-REFERENCE TO RELATED APPLICATION

This is a continuation of Ser. No. 07/616,058 filed Nov. 20, 1990, abandoned.

FIELD OF THE INVENTION

The invention concerns a method in X-ray diagnostics, in particular in mammography, for regulation of the exposure of a film or equivalent to an optimal level, in which method the radiation that has passed through the object of photography is measured by means of an arrangement of detectors and, based on this measurement, the time of exposure is regulated.

Further, the invention concerns a method in X-ray diagnostics, in particular in mammography, for carrying out automatic exposure, in which method a measurement signal is employed, which is compared with a reference signal during the time of exposure and, after the measurement signal has become equal to the reference signal, the radiation is switched off.

Further, the invention concerns a device in X-ray diagnostics, in particular in mammography, the device comprising a source of X-ray radiation, a film holder, a detector arrangement, by whose means the radiation that has passed through the object to be photographed is measured, and the device comprising a control unit which controls the various operations.

BACKGROUND OF THE INVENTION

In medical X-ray diagnostics both sharp contrast and high resolution are aimed at. At the same time, attempts are made to minimize the dosage of radiation received by the patient.

In X-ray photographing, in order to guarantee successful photographing irrespective of the quality of the object to be photographed and of the depicting apparatuses, it is known in prior art to provide the X-ray apparatuses with an automatic exposure system, which takes care of correct exposure of the X-ray film and thereby eliminates the necessity of renewed photographing.

In the prior-art automatic exposure systems, for example, an ionization chamber or a semiconductor has been used as the detector for the radiation passing through the film, the detector being placed behind the object to be photographed and behind the depicting means to measure the quantity of radiation arriving at the film. The signal, which is proportional to the radiation and suitably amplified, is linearized if necessary and thereupon integrated in relation to time. The result of integration is compared with the set value corresponding to the desired darkening of the film, and upon reaching of the value the radiation is switched off. In more advanced solutions, the creep of the base values of the detector and of the signal-processing stages have been compensated for by automatic resetting to zero, which is always carried out in between the photographings.

In relation to the present invention, reference is made to the FI Patent Applications Nos. 882490 and 894903 (applicant Automed Oy). The method and the device in accordance with the present invention can be applied particularly well expressly to the methods and devices described in the FI applications, in combination with which the present invention provides certain advantages of synergism.

In respect of the prior art most closely related to the present invention, reference is made to the FI Pat. Appl. No. 853317, to the DE Published Patent Application No. 36 41 992, and to the U.S. Pat. Nos. 3,974,385 and 4,763,343.

From the patent publications mentioned above, a method is known for regulating the exposure in a mammographic apparatus so that the radiation passing through the breast to be photographed is detected by means of one detector. In the U.S. Pat. No. 4,763,343 it is suggested that two detectors be employed, one of which measures the radiation passing through the tissue to be studied, whereas the other detector measures the radiation by-passing the tissue to be studied, the latter detector being used as a calibration signal for the regulation system. In the FI application 853317 it is suggested as a variation that, by means of one detector-in the automatic exposure system, a number of observations of the radiation passing through the organism and corrections of the spectrum are carried out one after the other during the photographing.

However, the prior-art solutions involve certain drawbacks, such as factors hampering the operation and the calibration, the object of the present invention being to eliminate the drawbacks.

One drawback present in prior-art solutions, in particular in mammographic photographing, is the fact that there is only one detector for measurement of exposure, which must be displaced to different locations depending on the size of the object to be photographed and on the projection of photography in order that correct exposure could be obtained.

As a rule, the displacement of the detector has been carried out manually, in which case the location of the detector and, thus, also the correct exposure must be taken care of by the operator of the mammographic apparatus. It can be justly considered that the reason for such a solution is the difficulty of calibration of the detector. If there are several detectors in stead of one, they all must be calibrated separately.

In the prior-art solutions, the creep of the base values of the signal-processing stages and of the detector has been compensated for by means of automatic resetting to zero, but possible alteration of the amplification has not been corrected. Since amplification of the signal has an essential importance for successful measurement and since the signal given by the detectors in relation to the amount of X-ray radiation varies considerably, in the prior-art solutions the calibration has always been carried out by adjusting the amplification by means of a regulation member manually, by test photography, and by measuring the darkening of the film. In such a case, the operation of regulation is difficult and time-consuming, for, as a rule, the regulation members are placed in the area of effect of radiation, which requires that the regulating person must always move to protection for the time of test irradiations. Also, such regulation members as well as the detector itself have a tendency of alteration in the long run, whereby the measurement result obtained no longer corresponds to the original setting and requires renewed calibration by a person skilled in the art.

Since the detector signal, e.g., in the case of semiconductor detectors does not correlate directly with the darkening of the film, but depends on the kV-value used for the X-ray tube, on the film type and amplification plates, on the cassette type, grid, filter type, and on the exposure time as the film sensitivity is lowered in accordance with the reciprocity law as the time becomes longer, a detector signal integrated in relation to time cannot be used directly for switching-off the radiation when the signal reaches the set value.

Thus, in more advanced prior-art automatic exposure systems, to improve the result, various value tables, stored in the memory of a microprocessor, have been used, in which tables, depending, for example, on the kV-value, filtration, and on type of film/amplification plate, the correct table value has been taken into use for switching-off the radiation. The measurement of such tables is highly laborious, they take an abundance of memory and program space, and their alteration is equally difficult as the creation of a new table. Thus, for the arrangement of measurement in accordance with the present invention, a novel mode of signal processing has been developed, which permits quick adapting of new types of films/amplification plates or of new filter materials even by the operator, and in the present invention just a few storage locations of memory space are required per each type combination.

The object of the present invention is to provide such a method and a device for automatic exposure in mammographic photography that different objects of photography can be photographed optimally with a sufficiently low dosage of radiation.

A further object of the invention is to provide a method and a device for automatic exposure in mammography, the method and device having versatile properties and being advantageous to accomplish.

SUMMARY OF THE INVENTION

In view of eliminating the above drawbacks and achieving the objectives stated above and those that will come out later, a first method in accordance with the invention is characterized in that the measurement signals are passed from the detector or from different detectors to the amplifier of each detector's own, and that, by means of the control system, which has been brought into a particular calibration state, the amplifications of the amplifiers are regulated to the levels required by the exposure of different objects of photography, and that, in the state of normal operation of the system, exposure measurement is carried out by making use of the amplification values adjusted in the way mentioned above.

On the other hand, a second method in accordance with the invention is characterized in that in the method a reference signal variable in relation to time is employed, the reference signal being defined by means of an initial value and of end points and of slopes between the end points, and that, when a new film type is being taken to use, the initial value and/or one or several of the slopes is/are changed.

On the other hand, the device in accordance with the invention is mainly characterized in that the device includes one or several radiation measurement detectors fitted in connection with, or at the proximity of, the film holder, each of the detectors being connected to the input of its own amplifier, that the control system is fitted to control the amplifications of the amplifiers, and that the outputs of the amplifiers are connected to a summing integration member or equivalent, which forms a signal by whose means the radiation is switched off.

In the solution in accordance with the present invention, the regulation of the amplification of the detector signal is arranged as a part of the control system that controls the X-ray apparatus, so that, when in a particular calibration state, the control system regulates the amplification to the correct level and, when in the normal operation state, the control system uses the amplification value obtained for carrying out the exposure measurement. In the solution, there are no creeping regulation members, and checking of the adjustment can be carried out quickly by the operator of the apparatus, and no specialized persons are needed.

In the solution in accordance with the present invention, the number of detectors need not be limited because of difficulty of calibration, but it is advantageously possible to use a necessary number of detectors in accordance with the requirements imposed by all expected objects and modes of photography, for the control system can quickly calibrate all of them.

It is an important additional advantage of the invention that, by separately adjusting the amplification of each of the detectors, in stead of one detector, it is possible to choose all the detectors or some accentuated partial area as the range of measurement, whereby, by shifting and/or altering the area of emphasis of the measurement, the measurement can be carried out much more accurately than in prior art, in consideration of the geometric and physiological properties of the object to be photographed.

The control system of the device can carry out the selection of a correct detector automatically in accordance with the size of the object of photography and with the mode of photography, which data are, in accordance with prior-art solutions, fed normally into the control system in order that it should place the photographing stand in the correct position and, when necessary, choose the correct kV- and mA-values of the source of X-ray radiation.

In the following, the invention will be described in detail with reference to some exemplifying embodiments of the invention illustrated in the figures in the accompanying drawing, the invention being by no means strictly confined to the details of the embodiments.

DESCRIPTION OF PREFERRED EMBODIMENTS

Figure 1:
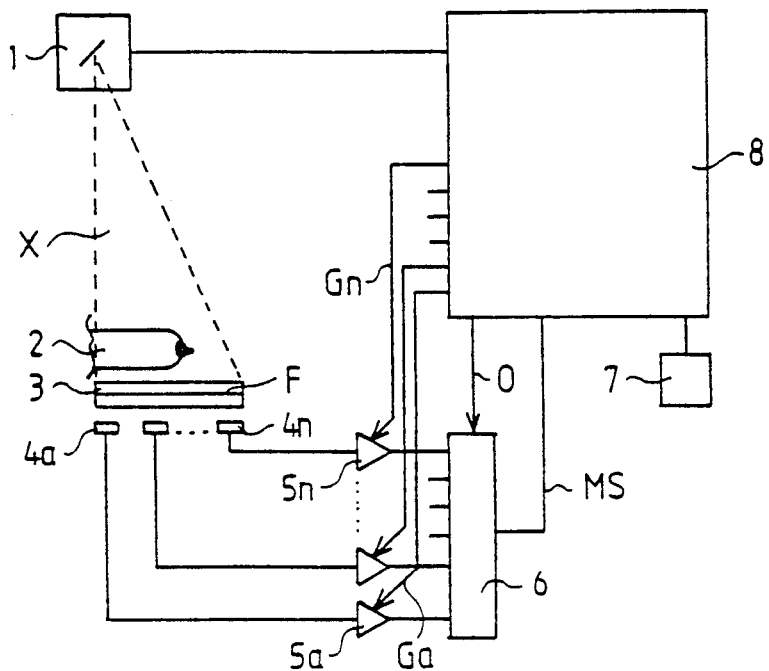
FIG. 1 shows the measurement and control system as a block diagram.

To begin with, the basic construction of the system illustrated in FIG. 1 will be described. The control system 8 switches on the X-ray radiation from the X-ray tube 1, whereby the radiation beam X passes through the object 2 to be photographed, e.g. the breast, and through the film cassette 3 to the film F placed in the cassette, forming a latent picture of the object 2 to be photographed on the film. The radiation beam X passes further to the detectors $4a \ldots 4n$ which measure the radiation. The signal given by each detector $4a \ldots 4n$, which is proportional to the radiation, is amplified by means of an amplifier 5a... 5n of its own, being then passed to a summing and integration member 6, from which the signal MS (FIG. 4), which is integrated in relation to time, is passed further as feedback to the control system 8. When the signal MS reaches the set-value level chosen by means of the setting member 7, the control system 8 switches off the radiation of the beam X.

Figure 3:
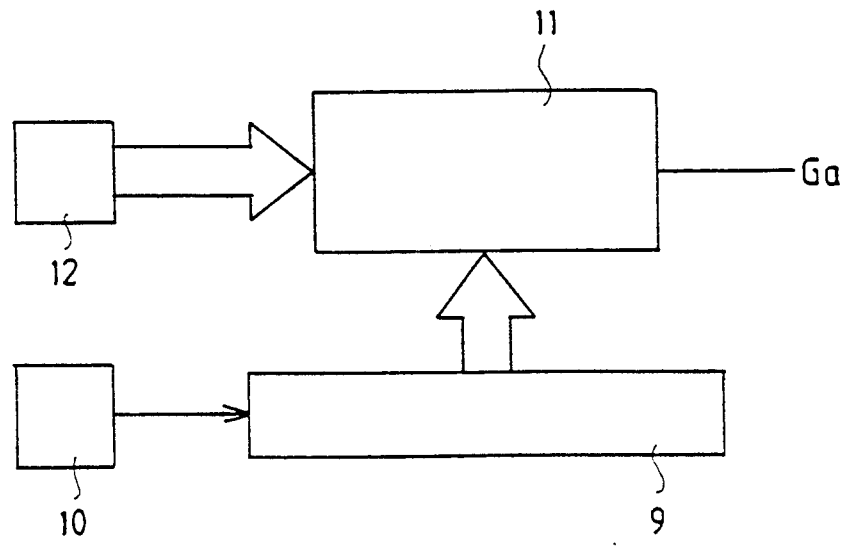
FIG. 3 illustrates the arrangement of an amplification regulation signal as a block diagram.
Figure 5:
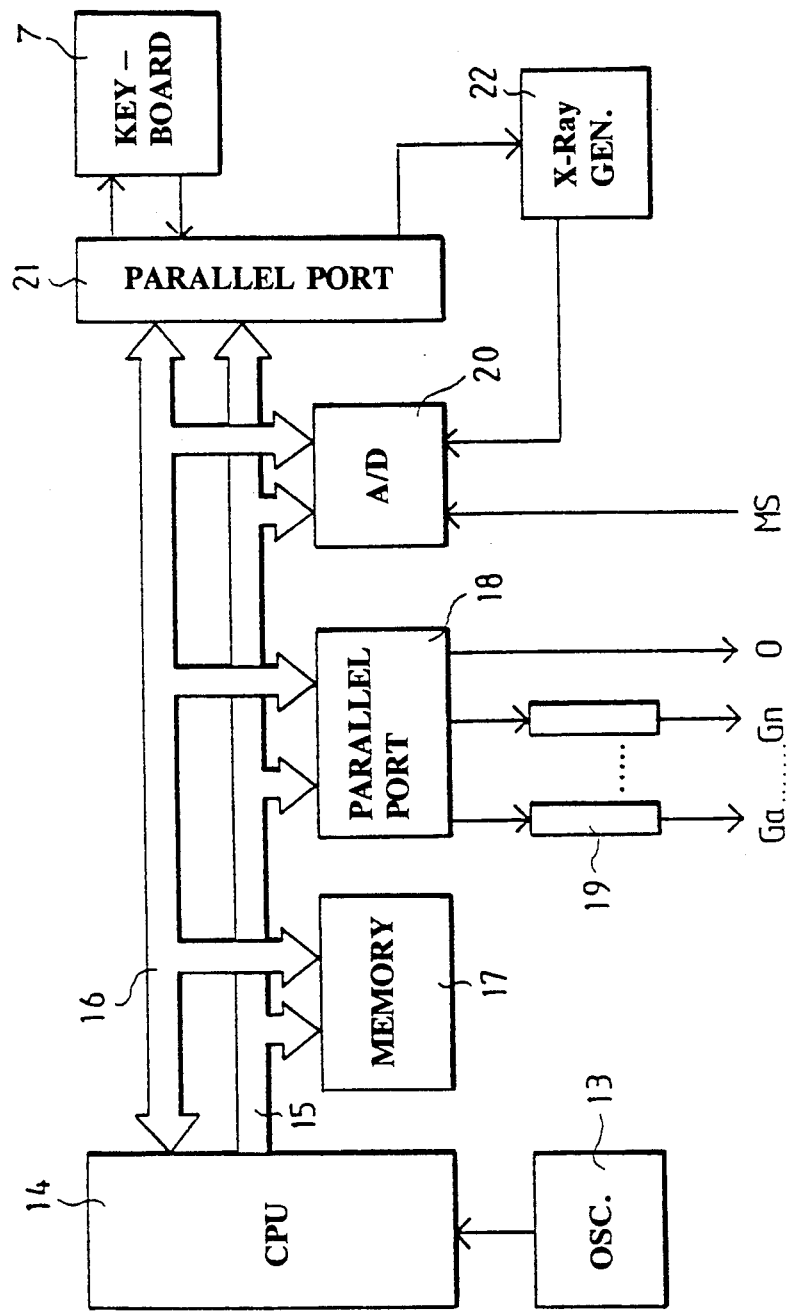
FIG. 5 shows the control system as a block diagram.

FIG. 5 shows a possible alternative embodiment of the control system 8. A clock oscillator 13 operates the microprocessor central unit 14, which is connected to the program memory 17 by means of an address bus 15 and a data bus 16, the execution programs of the system being stored in the program memory 17. Further, by means of buses, the microprocessor is connected to a parallel port 18, by whose means suitable set values are given to the pulse width generators 19, illustrated in more detail in FIG. 3, and, further, the zero signal 0 is controlled. By means of the parallel port 21, the microprocessor reads the keyboard 7 and controls the X-ray generator 22, from which the feedback is obtained by means of an analog/digital converter 20 to the microprocessor. The same converter is also used for converting the MS-signal to the digital form processed by the microprocessor.

There may be one or several detectors 4a... 4n and signal amplifiers 5a... 5n, but it is a characteristic feature that, in the control system, for each signal amplifier 5a... 5n a separate amplification control Ga... Gn of its own is fitted, by whose means the amplification in each amplifier 5a... 5n can be regulated within appropriate limits. Moreover, from the control system 8 to the summing and integration member 6, a zero control 0 is provided, by whose means the base value of the measurement signal is rest to zero before irradiation is started, so thatm for each signal amplifier 5a... 5n, the amplification value is given that is intended to be used in the photographing, and the integrator is allowed to be set to zero by means of this setting. The zero function is described in more detail below in the description related to FIG. 2, and, as regards its principle, it is in itself known in prior art.

Figure 2:
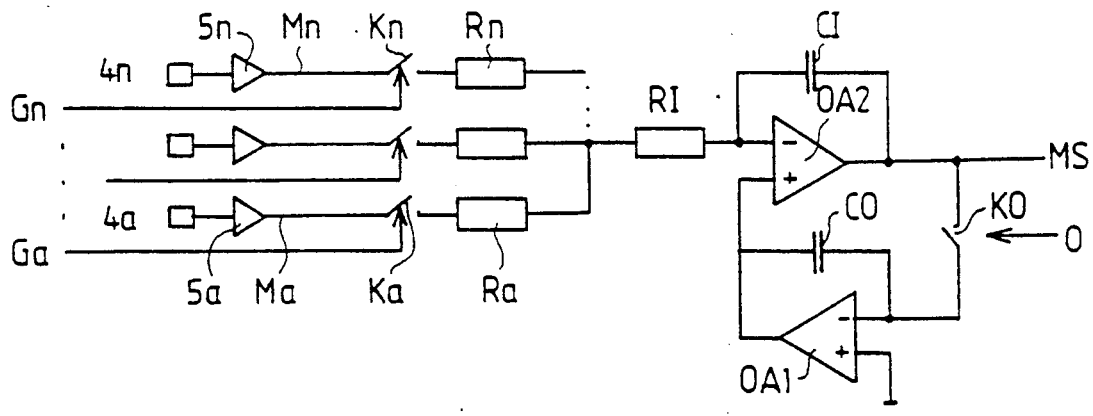
FIG. 2 shows the amplifier stages and the summing and integration stage.

FIG. 2 is a more detailed illustration of the amplification and integration stages. The integrator proper consists of an operation amplifier OA2, an integration capacitor CI, and an integration resistor RI. Before measurement operation, the base value is reset to zero by closing the switch KO by means of the control signal 0, at the same time as the detectors 5a... 5n to be used are switched on by the switches Ka... Kn by means of the control signals Ga... Gn intended to be used. Hereby, the voltage, if any, effective at the output of the integrator is charged by means of OA1 in the capacitor CO, and the measurement signal MS is reset to zero. During the measurement process proper the switch KO is open, whereby the value of the capacitor CO is not changed, but takes care of compensating for the base value that was measured earlier. When components with sufficiently low leakage flow are used, in practice, during the exposure, no error worth mentioning has time to take place owing to a change in the charge.

The integration of the measurement signal proper takes place during irradiation of the beam X. It is assumed, for example, that the detector 4a and the amplifier 5a alone are in operation, and the switch Ka has been closed by means of the amplification control signal Ga. Thereby the measured signal Ma is integrated through the resistor Ra+RI in the capacitor CI and is seen as the control signal MS in accordance with formula (1).

$$MS = -\int_{t_0}^{t_1} \frac{MA}{(Ra + RI)CI} dt \qquad (1)$$

The regulation of amplification is carried out by opening and closing the switch Ka by means of the control signal Ga with a suitable pulse ratio by using a switching frequency which is substantially higher than the time constant of the integrator. The pulse ratio used for switching the signals from each amplifier thus provides an initial integration time constant associated with that amplifier and applied to integrate the amplified measurement signals from that amplifier. By adjusting this time constant, i.e., changing the switching period, for a particular amplifier, the amplification of that amplifier thus is effectively adjusted for signals from that amplifier. Thus, for example, if the switch Ka is closed half the time only, the measurement signal MS is integrated as only one half of the earlier value, i.e. the amplification has been regulated to one half of the original. Further, when the control signal Ga is arranged in accordance with FIG. 3 from the reference circuit 11, which compares the value 12 that was set digitally with the value of the counter 9 operated by the frequency generator 10, a pulse ratio is provided which remains invariable, and no creep occurs. Even if the frequency provided by the frequency generator 10 were changed to some extent, that change does not affect the measurement result provided that the frequency remains substantially higher than the time constant of the integrator. In practice, it can also be stabilized easily, for example, by means of a crystal.

When several detectors and signal amplifiers are used, a resistor Ra... Rn and a switch Ka... Kn of its own are provided for each of them, the resistors and switches being controlled correspondingly by means of the signals Ga... Gn. In such a case, when only one switch is being switched, the measurement is carried out by means of one detector, but when several switches are switched, each of them expressly with a pulse ratio or integration time constant of its own, the measurement result that is obtained consists of a sum of several measurement signals weighted in a predetermined way.

In practice, the resistances Ra... Rn are chosen as substantially lower than the resistance Rl, the integration result being the average weighted with the amplifications of the chosen signals. For example, if the measurement signal Ma is 1 and Mb is 2 and the switches Ka and Kb are kept closed, at the switching point of the resistors Ra, Rb and RI a signal 1.5 is produced (since RI is substantially higher than Ra and Rb, its effect can be disregarded), which signal is then integrated through the resistor RI as the measurement signal MS. Thus, when the pulse ratios of the control signals Ga and Gb have been chosen so that, with the same radiation amount, the same integration result is obtained separately from each of them, the integration result of their average is obtained when they are used at the same time, i.e. the measurement is carried out from the area of two detectors as an average of the measurements, and not as a sum, which would give an incorrect result in view of the regulation of the exposure. Further, by changing the pulse ratios from the above ratios that give equal signals, the measurement can be weighted so that it comes from one detector 4 to a higher extent than from the other or, when a higher number of detectors 4 are used, in a suitable way from all 4a . . . 4n of them or from some of them.

Since the regulation of amplification has been accomplished digitally by means of the pulse ratio or integration time constant and is proportional to the pulse ratio used, in the control system it is easy to accomplish different weightings accurately.

Before the measurements proper, the detectors must be calibrated. For this purpose, the control system 8 is placed in a particular calibration operation, and in place of the object to be photographed some reference is placed, such as an amount of acrylic corresponding to an average breast. When the exposure switch 7 is pressed, the control system 8 carries out a short test irradiation with a certain kV-value of the source 1 of X-ray radiation and with a certain amount of mAs while employing a predetermined amplification value, for example 0.5, by using a corresponding integration time constant. On completion of the irradiation, the control system 8 measures the measurement signal MS obtained and compares it with a predetermined reference value, and corrects the pulse ratio or integration time constant of the amplification adjustment signal to such a level that, by its means, the correct signal value is obtained. If necessary, it is also possible to carry out a checking measurement with the value obtained. In this way the detectors 4a . . . 4b are calibrated one after the other while always running a resetting-to-zero cycle of the integrator in between. When sufficiently short exposure times are used, the calibration of the detectors can be carried out in a few seconds, for example, by the operator of the apparatus.

Since the radiation output of X-ray tubes varies to some extent from individual tube to tube and since, consequently, the correct degree of darkening of the film is not necessarily always achieved with the same object of photography and with the same kV- and mAs-values, for this purpose a possibility of correction can be added to the control system 8 even though the difference is so little that it need not necessarily be taken into account in practice. After calibration of the detectors 4a . . . 4n, a test photography of the above reference object is carried out on the film F, which is developed and whose darkness is measured. If the darkness differs from the given reference value, the control system is given a correction factor to adjust the initial integration time constant for the amplified signal from the particular amplifier, which eliminates the difference. For this regulation, a densitometer must be available for measurement of the darkness of the film, so that the operation is not entirely simple, but, on the other hand, it does not necessarily have to be carried out at all, or it must be carried out only once when the apparatus is being taken to use at the factory, and possibly after a long service to correct an altered radiation output of the X-ray tube.

As was stated in the initial part of the description, it is not possible to use the measurement signal MS described above for switching-off the radiation directly. To provide a correct exposure of the film, consideration must be given to the anode voltage (kV) used for the X-ray tube, the film/amplification plate type, the cassette type, the grid and the filtration, as well as, additionally, to the effect of the exposure time on the lowering of the sensitivity of the film. In the prior-art solutions, this has been accomplished by means of the above table formations, but in the following, particularly with reference to FIG. 4, a detailed description is given of a simple solution in accordance with the present invention, wherein the table required is so little that it can be stored in the changeable memory and can be even remembered by the operator, which has not been possible in the prior-art solutions.

Figure 4:
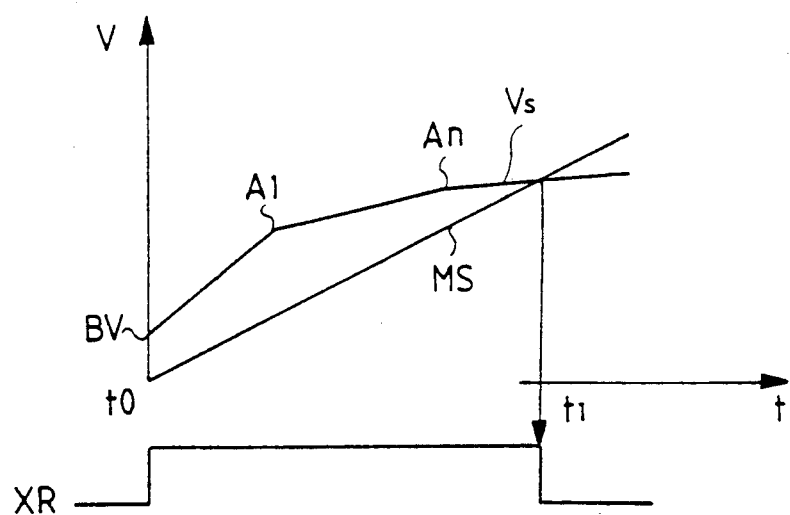
FIG. 4 illustrates the switching-off of radiation on the basis of comparison of the measurement signal.

FIG. 4 illustrates the comparison of the measurement signal MS with the reference signal VS in relation to time as well as the switched-on time $t_0$-$t_1$ of the radiation XR. It is seem from the figure that, when the radiation XR is switched on at the time $t_0$, the measurement MS integrated from the detector signal starts increasing in a linear way with time. Instead of comparing the value MS with a certain fixed table value at different points of time, upon reaching of which value the radiation is switched off, which was the case in the prior-art solutions, in the solution of the present invention a reference signal VS variable in relation to time has been provided which gives a linear approximation. In the solution in accordance with the invention, the reference signal VS is determined by means of the initial value or starting point BV and the end points $A_1$ . . . $A_n$ during exposure to the radiation, as well as by means of the slopes of the straight lines passing through those points. Thus, the curve of the reference signal VS in FIG. 4 is determined by its starting point BV, the first straight line passing through the starting points and the slope of this straight line, the end point $A_1$ of the first straight line, the second straight line starting at the end point $A_1$ and ending at the end point $A_n$, and the slope of that second straight line. These points BV, $A_1$ . . . $A_n$ and the slopes of the straight lines connecting the straight lines between the points provide the reference signal VS that is a linear approximation of the curves (not shown) between those points.

In practice, it has been noticed that a very high accuracy is achieved by means of determinations of the initial value BV and of two end points $A_1$ and $A_2$ when the end point $A_1$ is set as fixed at a certain moment in time. Thus, for example, the introduction of a new film type requires that a new initial value BV and two slopes for the end points $A_1$ and $A_2$ are fed in per each kV-value to be used. Since a typical kV-range of operation of a mammographic apparatus is 30 . . . 35 kV, a new film type requires 48 figures, whose conversation by the operator is fully possible, in stead of the several hundreds of values in the prior-art solutions. Moreover, since the values suitable for different kV-values behave in a predictable way, it is possible to feed only the values required by a few kV-values into the system, for example 20, 27 and 35 kV, from which the system automatically searches the suitable intermediate values for the other kV-values. By means of this method, it is really simple to introduce a new film type, the inputting of a few numerical values only being required. In the prior-art apparatuses, the introduction of a new film or filter type requires an expert on the site to enter new tables into the apparatus.

It should be emphasized strongly that, above, only some exemplifying embodiments of the invention have been given and that the scope of the invention also includes many modifications of the methods and devices of the invention which are obvious for a person skilled in the art, of which modifications just the following should be stated here: the switches for regulation of amplification can be substituted for by resistor of different sort with automatic control, different variations of the calibration function, or depicting methods in which, instead of a film F, some other method of storage of image is used, such as CCD-detectors.

In the following, the patent claims will be given, and the various details of the invention may show variation with the scope of the inventive idea defined in the claims and differ from the details described above.

What is claimed is:

1. Method in X-ray diagnostics, and particular in mammography, for regulation of the exposure of an image receptor (F) to an optimal level, wherein the radiation that has passed through an object (2) of photography and through the image receptor is measured by means of an arrangement of detectors (4a ... 4n) operative to produce measurement signals and, based on this measurement, the time of exposure or equivalent is adjusted, characterized by the steps of:

initially calibrating the detectors, amplifiers (5a ... 5n) associated with the detectors, and an integrator (6) by first zeroing the integrator and then exposing a reference object to a predetermined dosage of X-ray radiation to produce measurement signals from one or more of the detectors, one at a time;

passing the measurement signals from the detectors to the associated amplifiers to obtain an amplified measurement signal for each amplifier;

passing the amplified signals from each amplifier one at a time to the integrator, set to an initial integration switching period and zeroed between the measurements, to integrate the amplified measurement signals from each amplifier;

comparing the amplified and integrated measurement signals with a predetermined reference value and independently adjusting the switching period of each amplified signal being integrated to produce adjusted amplification values independently for each detector and its associated amplifier, so that at the predetermined dosage, each detector and amplifier gives an integrated measurement signal equal to the predetermined reference value; and thereafter exposing an unknown object to a dosage of X-ray radiation to produce measurement signals from the detectors;

automatically adjusting the switching period for the amplified signals from each detector and its associated amplifier by means of a control system in response to the adjusted amplification value obtained during the initial integration, as the amplified measurement signals for the unknown object are passed from the detectors to the amplifiers and to the integrator, so that the integrated result is a predetermined function of the amplified detector signals based on the adjusted amplification values determined during the calibration; and discontinuing the dosage of radiation to the unknown object when the integrated measurement signals reach a predetermined target value selected to be the intended dosage for the unknown object.

2. Method as in claim 1, wherein the adjusted amplification values are adjusted by opening and closing switches (Ka ... Kn) associated with the output of each amplifier (5a ... 5n) by means of a control signal (Ga ... Gn) with a preset pulse ratio at a switching frequency that is substantially higher than the time constant values for the integrator.

3. Method as in claim 1, comprising the further step of connecting the outputs of the amplifiers (5a ... 5b) of each of the detectors (4a ... 4n) by means of switches (Ka ... Kn), which are connected to a common resistor (RI) whose resistance is substantially higher than the resistance of said resistors (Ra ... Rn) so that an average weighted with the amplifications of the chosen detector signals is obtained as the integration result.

* * * * *